US00PP15663P2

(12) United States Plant Patent
Zimmermann

(10) Patent No.: US PP15,663 P2
(45) Date of Patent: Mar. 15, 2005

(54) HOP PLANT NAMED 'YCR ACCESSION NO. 4'

(50) Latin Name: *Humulus lupulus*
Varietal Denomination: YCR Accession No. 4

(75) Inventor: Charles E. Zimmermann, Prosser, WA (US)

(73) Assignee: Select Botanicals Group, L.L.C., Toppenish, WA (US)

( * ) Notice: Subject to any disclaimer, the term of this patent is extended or adjusted under 35 U.S.C. 154(b) by 26 days.

(21) Appl. No.: 10/326,830

(22) Filed: Dec. 20, 2002

Related U.S. Application Data

(60) Provisional application No. 60/343,939, filed on Dec. 27, 2001.

(51) Int. Cl.[7] ..... A01H 5/00

(52) U.S. Cl. ..... Plt./236

(58) Field of Search ..... Plt./236

*Primary Examiner*—Anne Marie Grunberg
(74) *Attorney, Agent, or Firm*—Stratton Ballew PLLC

(57) ABSTRACT

A new hop plant (*Humulus lupulus*) is disclosed. The new variety is used for its aromatic properties. The new variety is moderately tolerant to powdery mildew, and produces a medium size moderately compact cone with good pickability and storageability. The cones mature relatively late, and produce an exceptional yield of approximately 2200 to 3000 pounds per acre (2466 to 3363 kg/ha).

5 Drawing Sheets

Latin name of the genus and species of the plant claimed: *Humulus lupulus.*
Variety denomination: 'YCR Accession No. 4'.

STATEMENT REGARDING FERERALLY SPONSORED RESEARCH OR DEVELOPMENT

None.

BACKGROUND OF INVENTION

This invention relates to a new and distinct variety of hop plant (*Humulus lupulus*), and more particularly to a new hop plant resulting from the open pollination of 'Swiss Tettnanger' (unpatented) as part of a controlled breeding program in 1998. Selection of the new variety and initial reproduction by root cuttings was carried out in a research nursery in Prosser, Wash., U.S.A. Subsequent asexual reproduction took place in Granger, Wash., U.S.A. The new variety has been stably reproduced over successive generations.

Both 'YCR-4' and its parent 'Swiss Tettnanger' are classified as aroma hops, selected for desirable aroma quality. However, 'YCR-4' is distinguished from its parent 'Swiss Tettnanger' by several characteristics, as set forth in Table 1.

TABLE 1

Comparison of 'Swiss Tettnanger' and 'YCR-4'

| Characteristics | 'Swiss Tettnanger' | 'YCR-4' |
|---|---|---|
| Brewing quality | | |
| Average alpha acid level (percent of cone weight) | 4–6% | 6–9% |
| Average beta acid level (percent of cone weight) | 3–6% | 6–8% |
| Ratio of alpha acid to beta acid | 1:1 | 1:1 |
| Average cohumulone level (percent of alpha acid) | 20–25% | 26–29% |
| Total oils (ml/100 g) | 0.42–1.13 | Approx. 1.5 |

TABLE 1-continued

Comparison of 'Swiss Tettnanger' and 'YCR-4'

| Characteristics | 'Swiss Tettnanger' | 'YCR-4' |
|---|---|---|
| Storage quality | | |
| Stability (percent loss of alpha acids after 6 months storage at room temperature) | 50% | 20–30% |
| Agronomics | | |
| Yield (lbs./acre) | 1000–1300 | 2200–3000 |
| Susceptibility to powdery mildew | More susceptible | Less susceptible |
| Resistance to downy mildew | Moderate | Moderate |
| Maturity date (Yakima Valley, Washington) | Early, 3rd to 4th week of August | Late, 2nd week of September |

BRIEF DESCRIPTION OF THE PHOTOGRAPHS

DETAILED DESCRIPTION OF THE VARIETY

Figure 1:
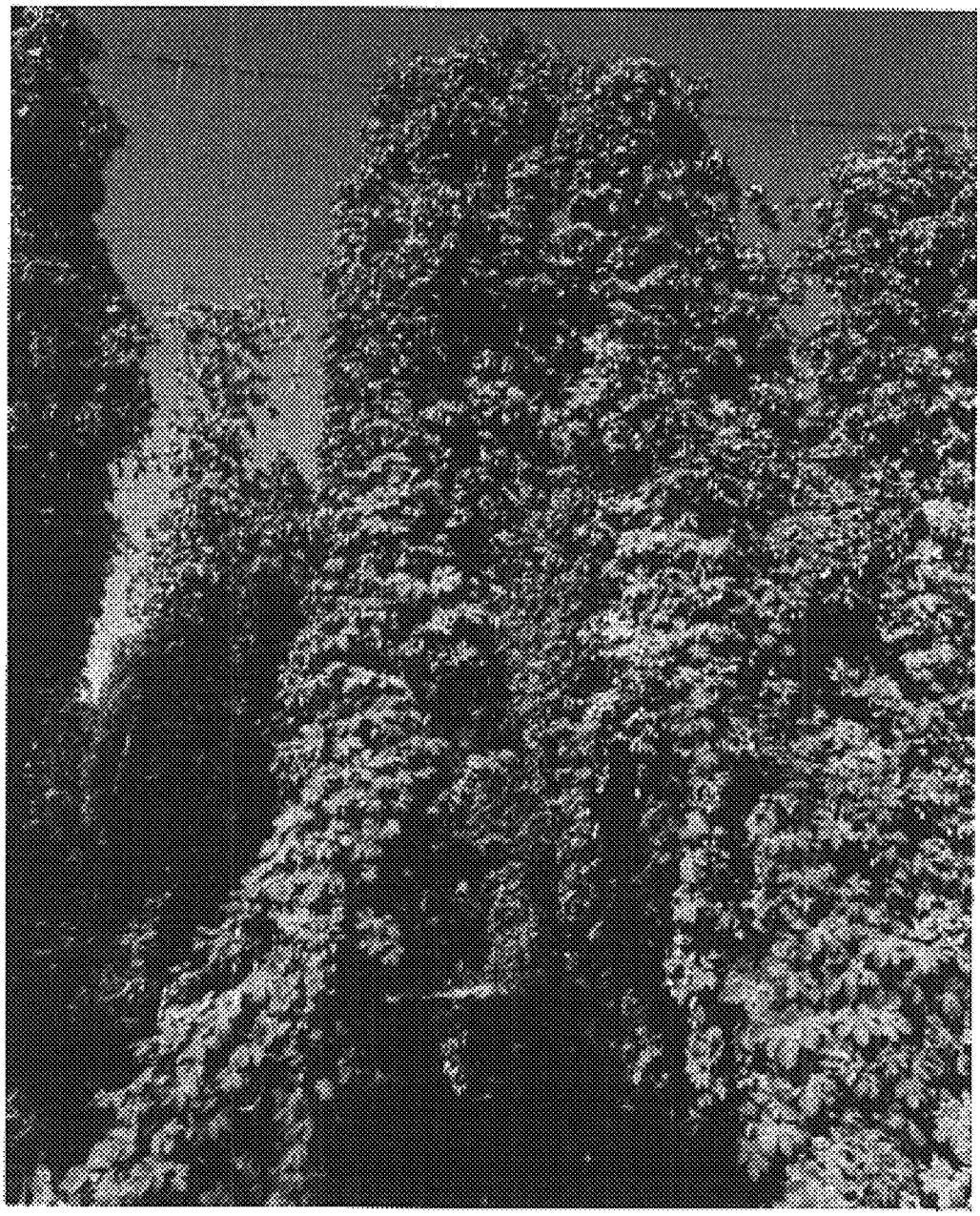
FIG. 1 shows a hop plant of the new variety.
Figure 2:
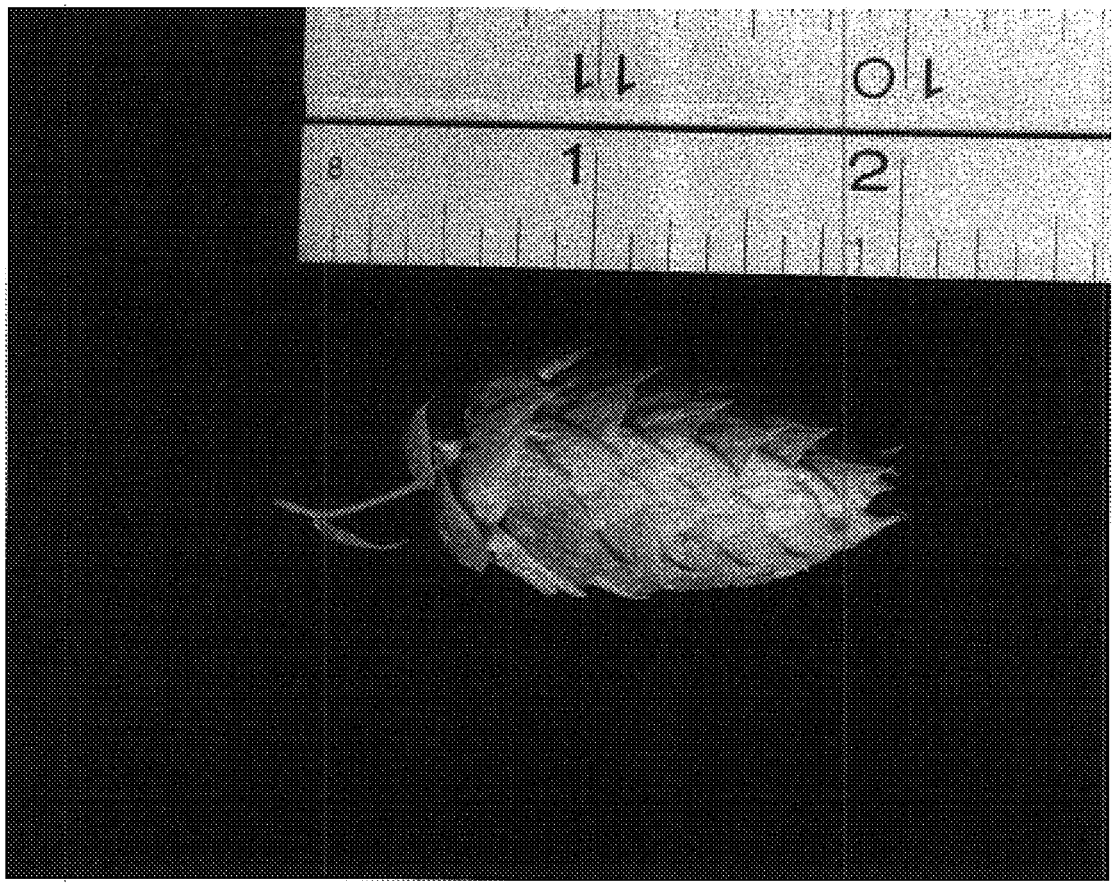
FIG. 2 shows a cone from a hop plant of the new variety.
Figure 3:
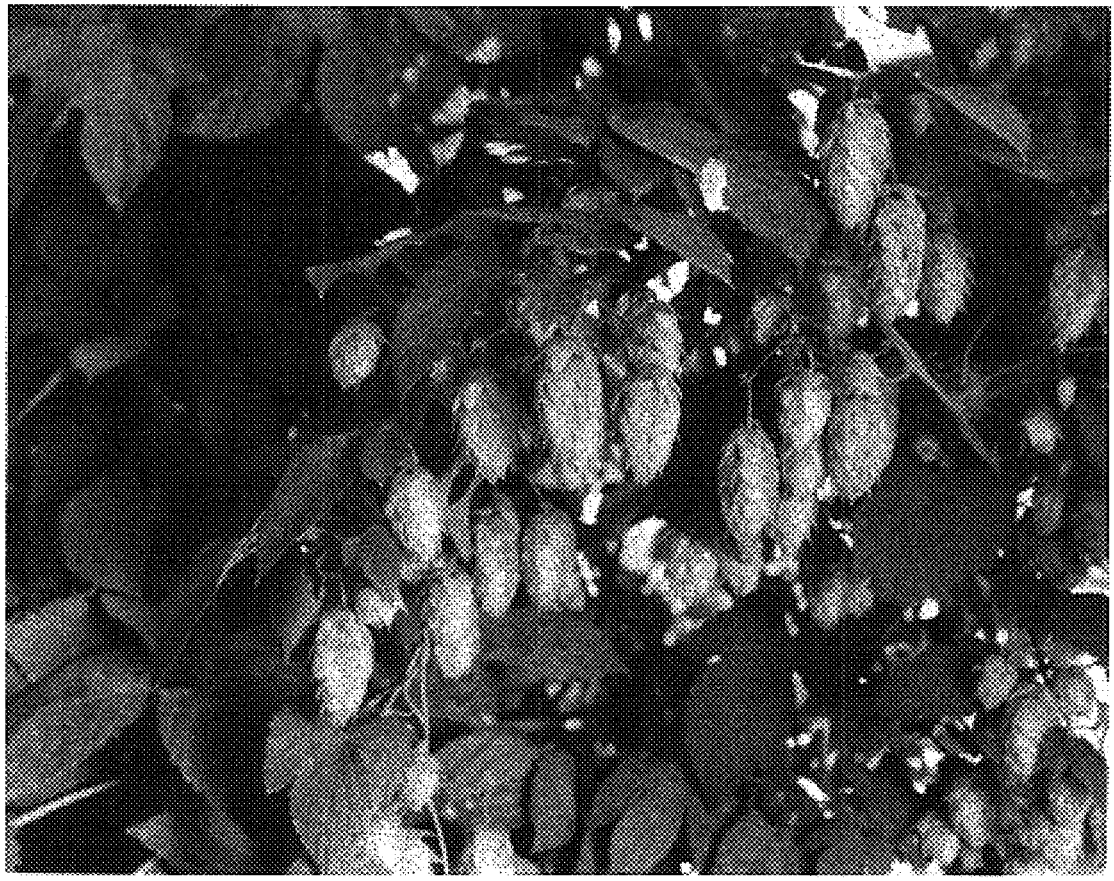
FIG. 3 shows a cluster of cones on a hop plant of the new variety.
Figure 4:
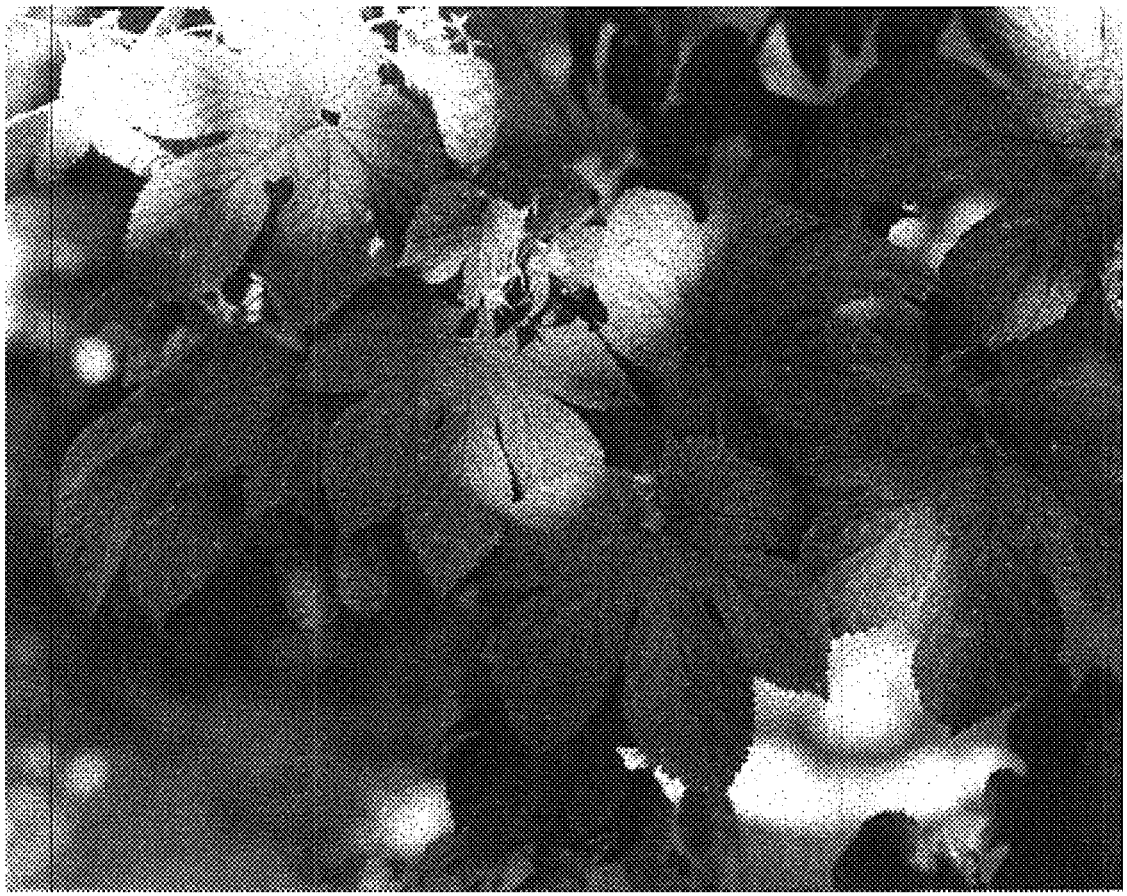
FIG. 4 shows the leaves of the hop plant of the new variety.
Figure 5:
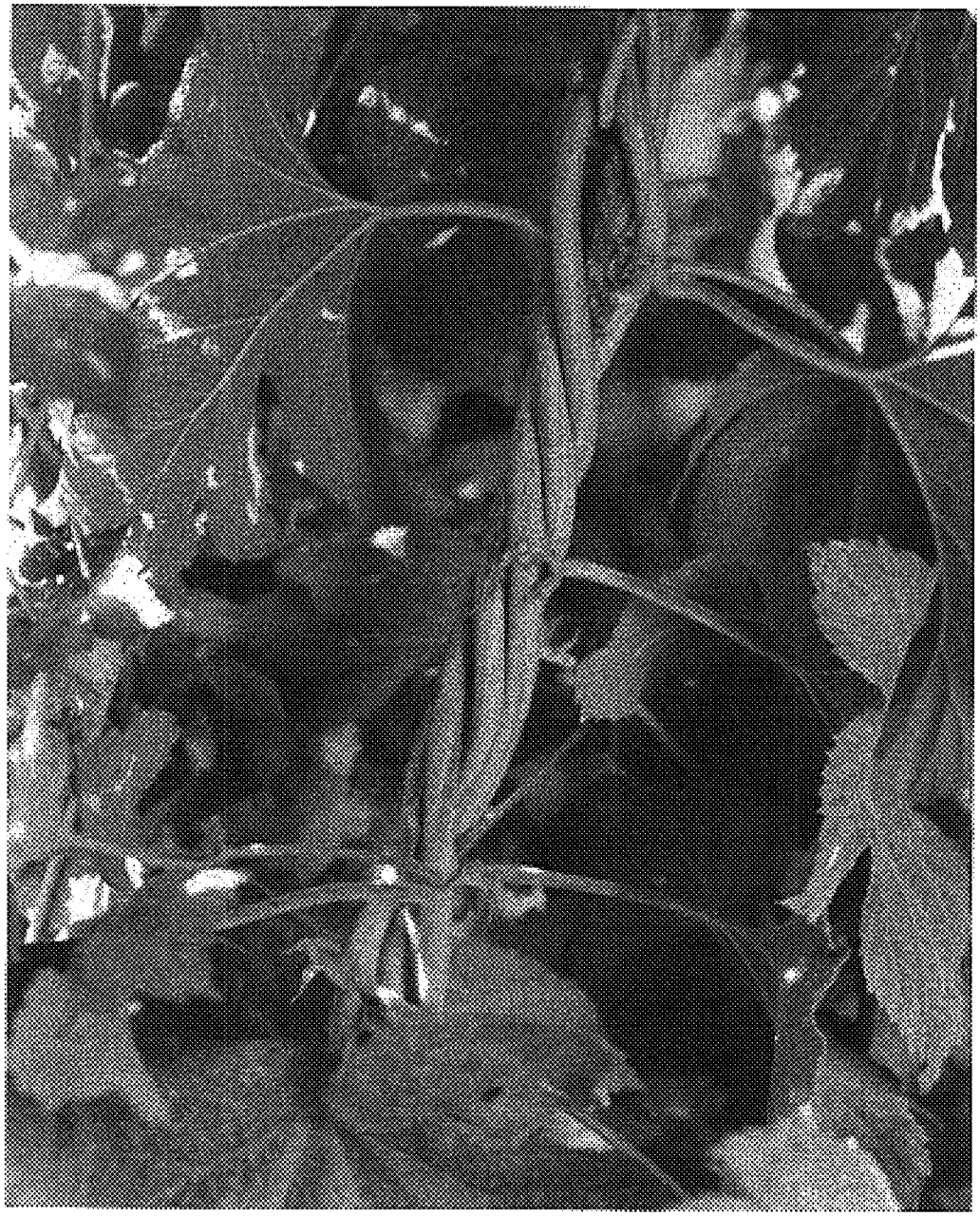
FIG. 5 shows the vine of the hop plant of the new variety.

The following is a detailed botanical description of the new hop plant, based on observations of specimens grown in Granger, Toppenish, Moxee, and Harrah, Wash. during the 2001 growing season. All colors are described according to The Royal Horticultural Society Colour Chart (Royal Horticultural Society, London). It should be understood that the botanical and analytical chemical characteristics described will vary somewhat depending upon cultural practices and climatic conditions and can vary with location and season.

Bine:

*Main bine color.*—146D yellow green.

*Stripe color.*—183C greyed purple.

*Stipule direction.*—Outward-down, forked.

*Stipule color.*—144B yellow green.

*Bine diameter.*—At base: 0.7 cm; 9 feet from base: 0.8 cm; 18 feet from base: 0.7 cm.

Leaves:

*Arrangement.*—Opposite.

*Shape.*—Palmate.

*Length.*—Avg. 14.5 cm (mature leaf).

*Width.*—Avg. 13.0 cm (mature leaf).

*Color.*—Upper surface, mature leaf: 137A green. Lower surface, mature leaf: 137C green. Upper surface, immature leaf: 137B green. Lower surface, immature leaf: 137C green.

*Number of lobes.*—3–10.

*Margin.*—Serrated.

*Serrations per inch.*—6–7.

*Pose.*—Downward.

*Petiole length.*—Avg. 6.4 cm (mature).

*Petiole color at base.*—Varied, 183C greyed purple and 143A green.

*Venation.*—Reticulate.

*Vein color.*—145A yellow green.

*Leaf resin gland color.*—13C, 14C and 15D yellow.

Cones:

*Length.*—Avg. 3.02 cm.

*Diameter.*—Avg. 1.63 cm.

*Bract tip color.*—146B yellow green.

*Bract base color.*—145B yellow green.

*Bracteole color.*—145B yellow green.

*Cone shape.*—Ovoid.

*Bract shape.*—Ovate.

*Bract tip shape.*—Cuspidate.

*Bract tip position.*—Recurved.

*Bracteole shape.*—Narrowly rounded.

*Lupulin gland color.*—17A, 17B, 15A and 15B yellow.

Quality data:

*Alpha acids (% of cone weight).*—5.46–9.29 mean=7.44, n=10.

*Beta acids (% of cone weight).*—5.78–7.79 mean=7.14, n=10.

*Cohumulone (% of alpha acids).*—24.88–29.09 mean=26.95, n=8.

*Total oils.*—1.5 ml/100 g cones.

*Storageability.*—70.25%–78.03% alpha remaining about 6 months storage at room temperature.

*Oil analytical data.*—Table 2.

TABLE 2

Essential Oil Profile of YCR4
106 mg of 10% Adsorbate/150 C/5 Min./1.0 ug Int. Std. By DTD-GC-MS
(Peak Area Integration from DTD-GC-FID Analysis)

| MS Spec # | Peak Assignment | GC-FID Peak Area | Area % |
|---|---|---|---|
| 92 | isoprene | 3154.714 | 1.493 |
| 198 | 2-methyl-3-buten-1-ol | 1457.541 | 0.690 |
| 296 | d-8 toluene (internal standard) | | |
| 328 | 3-methyl-2-butenal | 941.346 | 0.446 |
| 334 | n-octane | 798.296 | 0.378 |
| 339 | acetic acid | 1883.299 | 0.891 |

TABLE 2-continued

Essential Oil Profile of YCR4
106 mg of 10% Adsorbate/150 C/5 Min./1.0 ug Int. Std. By DTD-GC-MS
(Peak Area Integration from DTD-GC-FID Analysis)

| MS Spec # | Peak Assignment | GC-FID Peak Area | Area % |
|---|---|---|---|
| 370 | isobutyric acid (2-methylpropanoic acid) | 244.107 | 0.116 |
| 398 | possibly pentyl alcohol | 104.691 | 0.050 |
| 405 | 3-methylbutyric acid | 301.569 | 0.143 |
| 412 | 2-methylbutyric acid | 269.756 | 0.128 |
| 414 | 2-methyl-2-butanol acetate + 2,6-dimethyl-2,4-heptadiene | 299.401 | 0.142 |
| 422 | butyl-2-methylpropanoate (butyl isobutyrate) | 266.414 | 0.126 |
| 433 | alpha-pinene | 126.371 | 0.060 |
| 448 | possibly formamide | 1261.861 | 0.597 |
| 464 | beta-pinene + 2-methylbutyl propanoate | 821.842 | 0.389 |
| 468 | methyl, 5-methylhexanoate | 97.371 | 0.046 |
| 476 | myrcene | 20782.279 | 9.837 |
| 484 | hexanoic acid | 368.963 | 0.175 |
| 490 | 3-methylbutylisobutyrate | 1176.898 | 0.557 |
| 493 | 2-methylbutylisobutyrate | 1034.212 | 0.490 |
| 501 | alpha-phellandrena | 346.454 | 0.164 |
| 508 | alpha-terpinene | 507.470 | 0.240 |
| 515 | cis-ocimene | 354.921 | 0.168 |
| 523 | methylheptanoate | 413.171 | 0.196 |
| 533 | heptyl acetate | 283.440 | 0.134 |
| 542 | methyl, 6-methylheptanoate | 748.568 | 0.354 |
| 547 | heptanoic acid | 834.398 | 0.395 |
| 554 | linalool + pentyl-3-methylbutyrate | 2160.128 | 1.022 |
| 570 | methyl octanoate | 683.501 | 0.324 |
| 582 | methyl, 4-methyl-2-oxopentanoate | 451.766 | 0.214 |
| 591 | 2,3-dihydro-3,5-dihydroxy-6-methyl-4(H)-pyran-4-one | 684.438 | 0.324 |
| 604 | 2-nonanol | 339.230 | 0.161 |
| 617 | d-8 naphthalene (internal standard) | | |
| 623 | methyl nonanoate (branched isomer) | 2986.862 | 1.414 |
| 627 | methyl-4-octenoic acid | 870.192 | 0.412 |
| 635 | 2-decanol | 944.855 | 0.447 |
| 643 | methyl-6-nonenoate | 931.681 | 0.441 |
| 655 | methyl nonanoate | 1465.176 | 0.693 |
| 661 | nerol | 444.129 | 0.210 |
| 675 | 2-methylheptyl propionate | 881.313 | 0.417 |
| 681 | unknown | 230.901 | 0.109 |
| 686 | geraniol + 2-undecanone (branched isomer) | 1253.790 | 0.593 |
| 696 | 2-undecanol (branched isomer) | 338.728 | 0.160 |
| 705 | undecadienol isomer | 326.548 | 0.155 |
| 712 | undecenol isomer | 721.289 | 0.341 |
| 717 | methyl decanoate (branched isomer) | 1098.103 | 0.520 |
| 722 | 2-undecanone | 848.863 | 0.402 |
| 733 | 2-undecanol | 1262.099 | 0.597 |
| 740 | methyl-4-decenoate | 12898.897 | 6.105 |
| 742 | methyl-4,8-decadienoate | 579.773 | 0.274 |
| 755 | methyl geranate + methyl decanoate | 2548.231 | 1.206 |
| 766 | unknown | 204.564 | 0.097 |
| 777 | octyl-2-methylpropanoate | 756.305 | 0.358 |
| 784 | alpha-cubebene | 420.880 | 0.199 |
| 791 | 2-tridecanone (branched isomer) | 566.371 | 0.268 |
| 799 | 2-tridecanone (branched isomer) | 258.748 | 0.122 |
| 806 | methyl-2-undecenoate | 1041.976 | 0.493 |
| 808 | alpha-ylangene | 503.279 | 0.238 |
| 813 | alpha-copaene | 1203.824 | 0.570 |
| 826 | methyl undecanoate | 899.178 | 0.426 |
| 833 | 2-tridecanone | 507.088 | 0.240 |
| 843 | ? sesquiterpene 206 m.w. 163 base peak | 131.612 | 0.062 |
| 854 | methyl ester of unsaturated fatty acid | 136.607 | 0.065 |
| 867 | caryophyllene | 36181.296 | 17.125 |
| 874 | beta-cubebene | 2076.303 | 0.983 |
| 880 | linalylisobutyrate | 304.175 | 0.144 |
| 891 | 3-methylbutyloctanoate | 143.006 | 0.068 |
| 906 | humulene | 43184.507 | 20.440 |
| 913 | germacrene D | 407.641 | 0.193 |
| 928 | gamma-cadinene | 4751.493 | 2.249 |
| 940 | beta-selinene | 4255.554 | 2.014 |

TABLE 2-continued

Essential Oil Profile of YCR4
106 mg of 10% Adsorbate/150 C/5 Min./1.0 ug Int. Std. By DTD-GC-MS
(Peak Area Integration from DTD-GC-FID Analysis)

| MS Spec # | Peak Assignment | GC-FID Peak Area | Area % |
|---|---|---|---|
| 950 | alpha-selinene | 6501.117 | 3.077 |
| 955 | alpha-amorphene | 531.661 | 0.252 |
| 964 | methyl, 3,6-dodecadienoate | 544.689 | 0.258 |
| 972 | gamma-muuroline | 344.080 | 0.163 |
| 984 | delta-cadinene | 5902.935 | 2.794 |
| 993 | sesquiterpene w/ no common name CAS#16728-99-7, cadinene-type | 617.786 | 0.292 |
| 999 | alpha-muurolene | 696.655 | 0.330 |
| 1005 | alpha-calacorene | 123.304 | 0.058 |
| 1025 | 2-tetradecanone | 460.135 | 0.218 |
| 1030 | tetradecadienol isomer | 576.686 | 0.273 |
| 1037 | tetradecenol isomer | 993.396 | 0.470 |
| 1051 | caryophyllene oxide | 1378.781 | 0.653 |
| 1070 | methyl tridecenoate | 901.896 | 0.427 |
| 1076 | linalyl-3-methylbutyrate | 556.047 | 0.263 |
| 1082 | humulene oxide | 1253.453 | 0.593 |
| 1090 | unk. sesquiterpenol w/ 179 peak | 478.628 | 0.227 |
| 1105 | cadinol | 511.249 | 0.242 |
| 1110 | unk. sesquiterpenol w/ 179 peak | 563.546 | 0.267 |
| 1121 | delta-cadinol | 1236.734 | 0.585 |
| 1127 | beta-cadinol | 418.047 | 0.198 |
| 1136 | globulol | 1354.295 | 0.641 |
| 1144 | pentadecadienol | 3621.791 | 1.714 |
| 1155 | pentadecenol | 1431.673 | 0.678 |
| 1166 | unknown sequiterpenol | 496.377 | 0.235 |
| 1188 | 2-pentadecanone | 446.201 | 0.211 |
| 1216 | possibly a linalool or geraniol ester | 465.789 | 0.220 |
| 1228 | pentadecadienyl acetate | 388.543 | 0.184 |
| 1239 | pentadecenyl acetate | 843.677 | 0.399 |
| 1252 | possibly famesol | 1016.391 | 0.481 |

TABLE 2-continued

Essential Oil Profile of YCR4
106 mg of 10% Adsorbate/150 C/5 Min./1.0 ug Int. Std. By DTD-GC-MS
(Peak Area Integration from DTD-GC-FID Analysis)

| MS Spec # | Peak Assignment | GC-FID Peak Area | Area % |
|---|---|---|---|
| 1271 | myristic acid | 994.397 | 0.471 |
| 1361 | possibly famesyl acetate | 488.532 | 0.231 |
| 1371 | 2,4-heptadecadione | 158.692 | 0.075 |
| 1378 | hexadecadienol | 588.667 | 0.279 |
| 1416 | unknown | 176.575 | 0.084 |
| 1470 | 3,7,11,15-tetramethylhexadecapentaene isomer (272 m.w.) | 1016.312 | 0.481 |
| 1491 | palmitic acid | 1433.655 | 0.679 |
| | Total | 211276.645 | 100.000 |

Aroma profile: Mild, with citrus, spicy, floral, and piney notes.

Use: Used primarily in brewing for its aromatic properties.

Disease resistance:

*Powdery mildew.*—Moderate to high resistance.

*Downy mildew.*—Unknown; no infection observed to date.

*Verticillium wilt.*—Unknown.

Pickability: Good.

Harvest maturity: Late; after September 10.

Yield: 2200–3000 lb/ac (2466–3363 kg/ha) estimate.

I claim:

1. A new variety of hop plant substantially as herein shown and described.

* * * * *